(12) United States Patent
Hanft

(10) Patent No.: US 10,575,596 B2
(45) Date of Patent: Mar. 3, 2020

(54) PROTECTIVE PATIENT FOOTWEAR SYSTEM AND METHODS

(71) Applicant: MODERN PROTECTIVE FOOTWEAR, LLC, South Miami, FL (US)

(72) Inventor: Jason R. Hanft, South Miami, FL (US)

(73) Assignee: MODERN PROTECTIVE FOOTWEAR, LLC, South Miami, FL (US)

(*) Notice: Subject to any disclaimer, the term of this patent is extended or adjusted under 35 U.S.C. 154(b) by 0 days.

(21) Appl. No.: 16/055,628

(22) Filed: Aug. 6, 2018

(65) Prior Publication Data
US 2018/0343981 A1 Dec. 6, 2018

Related U.S. Application Data

(63) Continuation-in-part of application No. 14/853,417, filed on Sep. 14, 2015, now abandoned, which is a
(Continued)

(51) Int. Cl.
*A43D 3/00* (2006.01)
*A61B 5/00* (2006.01)
(Continued)

(52) U.S. Cl.
CPC ............ *A43D 119/00* (2013.01); *A43B 7/147* (2013.01); *A61B 5/1036* (2013.01); *A61B 5/112* (2013.01);
(Continued)

(58) Field of Classification Search
CPC .... A43D 2200/60; A43D 3/021; A43D 1/025; A61B 5/1074; A61B 5/6807; A61B 5/6829
See application file for complete search history.

(56) References Cited

U.S. PATENT DOCUMENTS

| | | |
|---|---|---|
| 4,745,290 A | 5/1988 | Frankel et al. |
| 5,195,030 A | 3/1993 | White |

(Continued)

FOREIGN PATENT DOCUMENTS

| | | |
|---|---|---|
| CN | 101088728 | 12/2007 |
| JP | 2001204512 | 7/2001 |

(Continued)

OTHER PUBLICATIONS

Piller, "Footwear Customization 3.0: The First Rapid Manufactured Shoe," Oct. 24, 2006, http://mass¬customization.blogs.com/mass_customization_open_i/2006/10/footwear_custom.html, pp. 1-3.
(Continued)

*Primary Examiner* — Ronald D Hartman, Jr.
(74) *Attorney, Agent, or Firm* — Richard P. Gilly; Archer & Greiner, P.C.

(57) ABSTRACT

This disclosure relates to a computer-implemented system and related methods for the design, evaluation, and/or manufacture of protective patient footwear, such as shoes, braces, boots, casts, corrective footwear, and orthoses. The system includes suitable hardware, software, and related peripherals, which function to acquire data related to the patient's particular footwear needs, such as by image capture, including three-dimensional scanning. The system may also acquire data through other sources of input, such as through one or more sensors for detecting various physiologic parameters associated with the lower extremity, or through input of medical conditions, prior indicators, exam, analysis, lab results, or the like, such as through medical practitioner input or other input protocols. The various inputs may be suitably processed to generate output in the form of a design accommodation to design or modify the protective patient footwear, or in the form of one or more medical evaluations or recommendations.

17 Claims, 7 Drawing Sheets

Related U.S. Application Data continuation of application No. 13/804,268, filed on Mar. 14, 2013, now Pat. No. 9,201,413.

(51) Int. Cl.
| | |
|---|---|
| *A43D 119/00* | (2006.01) |
| *G05B 15/02* | (2006.01) |
| *A61B 5/11* | (2006.01) |
| *A61B 5/103* | (2006.01) |
| *A43B 7/14* | (2006.01) |
| *G05B 19/42* | (2006.01) |
| *A43D 1/02* | (2006.01) |
| *A43B 7/28* | (2006.01) |
| *A43B 3/00* | (2006.01) |
| *A61B 5/01* | (2006.01) |
| *A43B 13/14* | (2006.01) |
| *A61B 5/22* | (2006.01) |
| *A43B 13/18* | (2006.01) |
| *A43B 17/00* | (2006.01) |

(52) U.S. Cl.
CPC ......... *G05B 15/02* (2013.01); *G05B 19/4207* (2013.01); *A43B 3/0005* (2013.01); *A43B 7/141* (2013.01); *A43B 7/28* (2013.01); *A43B 13/141* (2013.01); *A43B 13/188* (2013.01); *A43B 17/00* (2013.01); *A43D 1/02* (2013.01); *A43D 1/025* (2013.01); *A43D 2200/60* (2013.01); *A61B 5/01* (2013.01); *A61B 5/22* (2013.01); *G05B 2219/35036* (2013.01); *G05B 2219/45243* (2013.01); *Y02P 90/265* (2015.11)

(56) References Cited

U.S. PATENT DOCUMENTS

| | | | |
|---|---|---|---|
| 5,339,252 A | 8/1994 | White et al. | |
| 5,611,153 A | 3/1997 | Fisher et al. | |
| 5,659,395 A * | 8/1997 | Brown | A43D 1/025 33/3 R |
| 5,687,467 A * | 11/1997 | Bergmann | A43D 1/022 12/146 M |
| 6,205,230 B1 * | 3/2001 | Sundman | A61B 5/0064 382/100 |
| 6,315,786 B1 | 11/2001 | Smuckler | |
| 6,463,351 B1 | 10/2002 | Clynch | |
| 6,735,547 B1 * | 5/2004 | Yfantis | A43D 1/025 702/155 |
| 7,206,718 B2 | 4/2007 | Cavanagh et al. | |
| 7,409,256 B2 | 8/2008 | Lin et al. | |
| 7,493,220 B2 | 2/2009 | Leigh et al. | |
| 7,493,230 B2 | 2/2009 | Schwartz et al. | |
| 7,661,170 B2 | 2/2010 | Goode et al. | |
| 7,926,363 B2 | 4/2011 | Miller et al. | |
| 8,005,558 B2 | 8/2011 | Waatli et al. | |
| 8,596,145 B2 | 12/2013 | Miller | |
| 10,004,428 B2 | 6/2018 | Everett et al. | |
| 2001/0020222 A1 | 9/2001 | Lee et al. | |
| 2001/0030297 A1 * | 10/2001 | Milioto | A43D 1/025 250/559.22 |
| 2002/0120531 A1 | 8/2002 | Fonsen | |
| 2002/0158259 A1 | 10/2002 | Ono et al. | |
| 2002/0158358 A1 | 10/2002 | Franzene | |
| 2004/0133431 A1 | 7/2004 | Udiljak et al. | |
| 2004/0168329 A1 | 9/2004 | Ishimaru | |
| 2005/0049816 A1 | 3/2005 | Oda et al. | |
| 2005/0061332 A1 * | 3/2005 | Greenawalt | A43D 1/025 128/882 |
| 2005/0171456 A1 | 8/2005 | Hirschman et al. | |
| 2005/0261869 A1 | 11/2005 | Leyerer et al. | |
| 2006/0143839 A1 | 7/2006 | Fromme | |
| 2006/0247892 A1 * | 11/2006 | Peterson | A43D 1/02 702/167 |
| 2006/0283243 A1 * | 12/2006 | Peterson | A61B 5/1036 73/172 |
| 2007/0038042 A1 | 2/2007 | Freeman et al. | |
| 2007/0039209 A1 | 2/2007 | White et al. | |
| 2007/0043582 A1 | 2/2007 | Peveto et al. | |
| 2007/0074430 A1 | 4/2007 | Coomer | |
| 2007/0245504 A1 | 10/2007 | Spector | |
| 2008/0010856 A1 | 1/2008 | Hakkala | |
| 2008/0104778 A1 | 5/2008 | Drake et al. | |
| 2008/0189194 A1 | 8/2008 | Bentvelzen | |
| 2009/0183388 A1 * | 7/2009 | Miller | A43B 7/141 36/43 |
| 2009/0247909 A1 * | 10/2009 | Mukumoto | A43B 7/28 600/592 |
| 2010/0030542 A1 * | 2/2010 | Boneh | A43D 1/025 703/11 |
| 2010/0130830 A1 | 5/2010 | Lin | |
| 2010/0275461 A1 | 11/2010 | Cook et al. | |
| 2011/0082578 A1 | 4/2011 | Stanhope et al. | |
| 2011/0099845 A1 | 5/2011 | Miller | |
| 2012/0198949 A1 * | 8/2012 | Xia | A43D 1/022 73/865.8 |
| 2013/0053677 A1 * | 2/2013 | Schoenfeld | A61B 5/1074 600/407 |
| 2014/0101134 A1 | 4/2014 | Bohrer et al. | |
| 2014/0182170 A1 | 7/2014 | Wawrousek | |
| 2015/0101134 A1 | 4/2015 | Manz et al. | |
| 2015/0165690 A1 * | 6/2015 | Tow | B33Y 80/00 700/119 |
| 2016/0081435 A1 * | 3/2016 | Marks | A43D 1/027 382/154 |
| 2016/0101572 A1 * | 4/2016 | Schouwenburg | B33Y 80/00 602/5 |
| 2016/0110479 A1 * | 4/2016 | Li | A43B 7/141 703/1 |
| 2017/0017230 A1 * | 1/2017 | Spector | A43B 17/00 |
| 2017/0027477 A1 * | 2/2017 | Charles | A61B 5/1036 |
| 2017/0079559 A1 * | 3/2017 | Ward | A61B 5/1078 |
| 2018/0279912 A1 * | 10/2018 | Penta | A61B 5/1072 |
| 2018/0343981 A1 * | 12/2018 | Hanft | G05B 15/02 |

FOREIGN PATENT DOCUMENTS

| | | | | |
|---|---|---|---|---|
| WO | WO-02061655 A1 * | 8/2002 | | A43B 7/141 |
| WO | WO2004073441 A1 | 9/2004 | | |
| WO | WO-2008070537 A2 * | 6/2008 | | A43D 1/025 |
| WO | WO2008070537 A2 | 6/2008 | | |

OTHER PUBLICATIONS

Tuck et al., "Rapid manufacturing facilitated customization," International Journal of Computer Integrated pp. 245-258, vol. 21, Issue 3, 2008.
Jang, Ho Kaun, "International Search Report and Written Opinion" Korean Search Authority for International Application No. PCT/US2014/022393, dated Jul. 28, 2014, 8 pages.
U.S. Appl. No. 61/739,346; Wawrousek, et al; 113 pages; filed Dec. 19, 2012.

\* cited by examiner

PROTECTIVE PATIENT FOOTWEAR SYSTEM AND METHODS

CROSS-REFERENCE TO RELATED APPLICATIONS

This application is a continuation-in-part of application Ser. No. 14/853,417, filed 14 Sep. 2015, which is a continuation of application Ser. No. 13/804,268, filed 14 Mar. 2013, now U.S. Pat. No. 9,201,413, the entire contents of which are incorporate herein by reference.

FIELD

This disclosure relates to a computer-implemented system and related methods for the design, evaluation, or manufacture of protective patient footwear, and in particular, to computer-implemented design and manufacturing systems for patients with foot or other orthopedic conditions requiring accommodation.

BACKGROUND

Current systems and methods for designing or manufacturing footwear for diabetics or other patients with podiatric or orthopedic needs are generally time consuming and antiquated. To the extent automation of footwear design or manufacturing has occurred, such systems and methods suffer from various drawbacks and disadvantages, and are not well-suited for the particular needs of diabetics and other patients with podiatric or orthopedic issues.

SUMMARY

In one possible implementation, a computerized system is suitably programmed to perform various steps or operations for evaluation of protective patient footwear for a lower extremity. The system includes a design engine implemented on a computer having programmable memory and at least one processor that executes instructions stored in the programmable memory. One or more sensors may be positioned relative to the lower extremity to detect at least one physiologic parameter of the lower extremity. The physiologic parameters include plantar pressure, friction, temperature, force, force direction, contact area, acceleration, movement, moisture, temperature, and elapsed time. The design engine is programmed to (a) receive input from the one or more sensors corresponding to one or more physiologic parameters detected; (b) determine whether the input comprises an out-of-range value for a given one of the physiologic parameters; and (c) in response to the determination, generate an output to address the out-of-range value.

The generated output may relate to either a design accommodation or a treatment recommendation (or both). Possible design accommodations may include either a proposed geometry or a proposed material for the protective patient footwear, and may be selected from a set of design accommodations pre-programmed to correspond to the physiologic parameter for which the out-of-range value was detected. The proposed geometry outputted by the system programming may take the form of dimensional changes or values for an insole or other aspects of the patient protective footwear.

According to another aspect of the system, multiple sensors are positioned on the insole of the protective patient footwear at predetermined sensor locations relative to the musculoskeletal structure of the lower extremity when the protective patient footwear is being worn. So, for example, the sensors may be positioned relative to the insole to detect a plurality of the physiologic parameters of the plantar surface of the lower extremity when supported by the insole. In such scenario, in response to the design engine determining that there is an out-of-range value at a first location that corresponds to the physiologic parameter of plantar pressure, design accommodations could be generated corresponding to the addition of material to increase the thickness of the insole at locations other than at the first location, the substitution of softer material at the first location, or the inclusion of friction-reducing material at the top of the insole. The design accommodation may have specific dimensions associated with the proposed addition of materials, and may generate output in the form of design parameters for use in subsequent design, manufacture, or related dimensional modifications.

Other potential design accommodations which the system is capable of generating may include an addition of insole material to fill voids from an amputation, a modification of materials under unamputated lower extremity portions to relieve lower extremity-related forces due to the amputation, inclusion of at least one of stiffer materials and more flexible materials relative to surrounding material of the protective patient footwear to address a gait abnormality related to the amputation.

In another possible implementation and operation, the design engine, upon receiving sensor readings of an out-of-range plantar pressure on the first metatarsophalangeal joint, would generate output of either a proposed alteration of material or geometry, that is, dimensions, to relieve the condition in the proposed or modified protective patient footwear. Inputs received by the system may be used as variables in the generation of the output to address the out-of-range value.

The system herein may be directed for patient use, and thus include a patient interface, through which one or more treatment recommendations are communicated. The programming may branch or otherwise process inputs by previous occurrence, severity, or other factors, so as to generate differentiated treatment recommendations or related actions transmitted to the patient.

In other variations, the system may include a medical practitioner interface, and suitable programming may generate medical evaluations for the medical practitioner to consider for the patient, or medical recommendations in a variety of forms for the medical practitioner to impart to the patient. The evaluations and recommendations would be generated by the system in response to receiving one or more out-of-range values, and processing them in relation to the magnitude or nature of the out-of-range value, or in relation to other sensor inputs, patient data, or other medical inputs. Output generated may factor in previous occurrences or severity.

The above-described evaluation system may include a computer-aided manufacturing subsystem programmed to receive the design accommodation when generated by the design engine and manufacture the protective patient footwear corresponding to the design accommodation.

Similarly, in addition to receiving input from one or more sensors, the system herein may include an image capture subsystem adapted to receive digital input related to the lower extremity and generate an outputted design, or image capture output which can be factored in to the output generated from sensor inputs.

Also disclosed herein are various computerized methods for evaluating a lower extremity to be fitted with protective patient footwear. One method includes detecting one or more physiologic parameter of the lower extremity, such as plantar pressure, friction, temperature, force, force direction, contact area, acceleration, movement, moisture, temperature and elapsed time. In response to receiving input corresponding to a physiologic parameter, a determination is made as to whether the input comprises an out-of-range value for the physiologic parameter; and in response to the determination, programming generates an output to address the out-of-range value. The output may consist of either a design accommodation or a treatment recommendation, including those discussed above with reference to the system disclosed herein.

In other operations, the step of receiving input corresponding to the physiologic parameter may involve receiving a plurality of discreet inputs for a plurality of the physiologic parameters from a plurality of locations in operative proximity to the lower extremity. Upon detection of out-of-range values, the location of the out-of-range value relative to the lower extremity and the magnitude of the out-of-range value outside of a range value of the corresponding physiologic parameter is determine. Thereafter, the step of generating suitable output to address the out-of-range values factors in one or more of the following: physiologic parameters detected at locations other than the location associated with the out-of-range value, input corresponding to previous occurrences of the out-of-range values, gate analysis values, and input indicating existence of at least one medical condition.

Further steps of methods disclosed herein may involve generating design accommodations in the form of data or files suitable for further processing by other system program modules, such as programming associated with a design engine or a computer-aided manufacturing subsystem. In addition, or alternatively, methods disclosed herein may involve treatment recommendations which may be transmitted to either a patient user interface or a medical practitioner user interface.

This disclosure also relates to a design and manufacturing system for protective patient footwear, as well as related methods. The system includes suitable hardware, software, and related peripherals, which function to acquire data related to the patient's particular footwear needs, such as by three-dimensional scanning. A design subsystem interfaces with the inputted data to permit the resulting design to reflect particular foot conditions in the design and subsequent manufacturing process. A virtual last creation subsystem may be included to process the design parameters received by the system. The virtual last subsystem may then generate output for use in producing, for example, by subsequent manufacture, a corresponding custom shoe, brace, boot, casts or other corrective footwear for use in at-risk patients, such as diabetics.

In one possible version, the data generated by the virtual last would in turn be input into an automated tool for fabricating the footwear. One such automated tool would be computer-driven manufacturing tool. The tool is programmable to create footwear using any suitable manufacturing techniques, including injection molding techniques or three-dimensional printing techniques, and could thereby be used to create a custom, accurate product. The materials used for the resulting custom footwear may include, but not be limited to: open and closed cell foams, hybrid foam, EVA, cyanoacrylates, low friction cloth, Gore-tex, neoprene, rubber, plastics, paper, steel and carbon fiber. Quality and accuracy of the final product will be digitally compared to the original scan to validate accuracy of the final product.

In one implementation, the design and manufacturing system for protective patient footwear comprises distinct subsystems, and suitable physical and logical interconnections between such subsystems to integrate the scanning, design, and manufacturing steps in an efficient manner. The subsystems and related interfaces may be designed so that they are interchangeable and thus adaptable to different retail and office environments, as regards input of the design, and can likewise be interchangeable with different CAD or CAM software subsystems in connection with the generation of the virtual last and subsequent manufacture. As such, the system of the present disclosure may be based, at least partially, on commercially available 3-D scanning systems, as well as commercially available CAD/CAM systems and mold making and injection molding subsystems. The foregoing systems, however, are adapted and modified to not only integrate and streamline the process of procuring customized footwear for patients' foot conditions, but also the systems are able to accommodate particular foot conditions in a straightforward manner either in response to detection of such conditions or suitable input from medical practitioners during the design process.

When the system is configured to generate a virtual last prior to manufacturing, then the customized or particular needs are reflected in the generation of the virtual last. In other configurations, the customized or particular needs may be data output to the computer-driven manufacturing system, in those cases where a virtual last is not part of the system. Regardless of the exact system configuration, the disclosed system is able to accommodate the particular needs or conditions identified during consultation, scanning or other interaction with any number of medical practitioners or professionals, in a straightforward manner, and in turn allows for the ultimate manufactured footwear to address such needs or conditions.

DESCRIPTION

Figure 1:
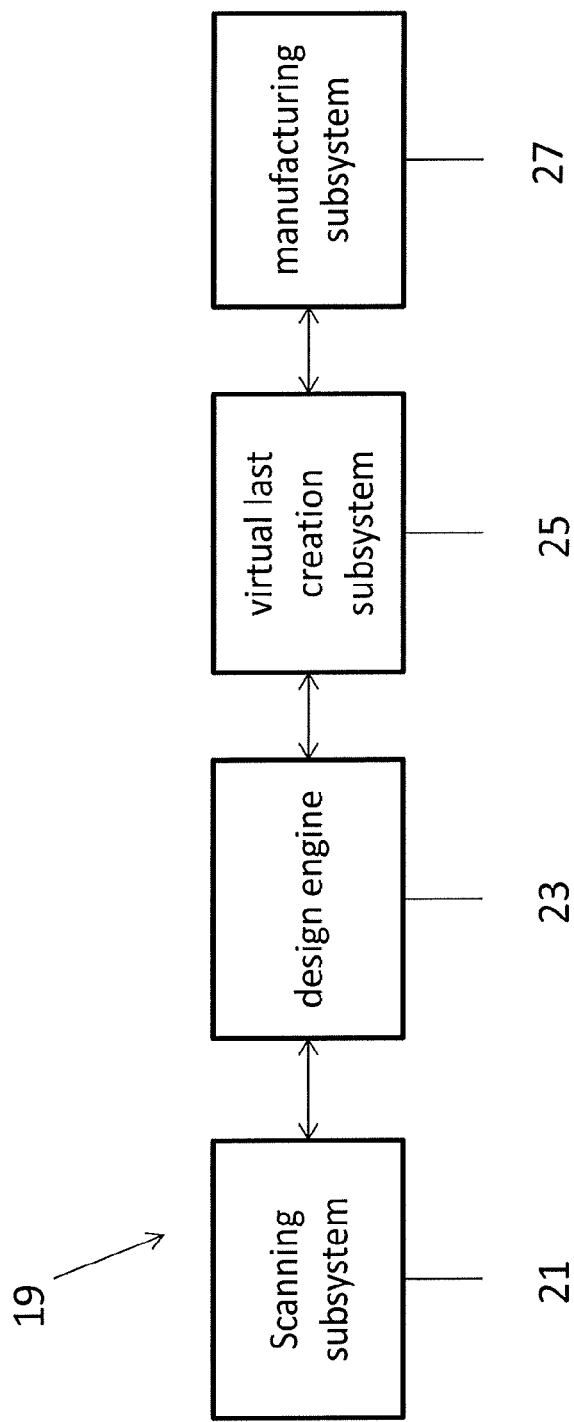
FIG. 1 is a schematic of one possible implementation of the present disclosure.

One possible implementation of a design and manufacturing system for protective patient footwear 19 is shown in FIG. 1. Scanning subsystem 21 receives suitable input related to a patient's foot or ankle. The scanning subsystem makes use of a suitable user interface so that it can be used by the medical practitioner, whether a medical technician, orthotists, pedorthist, orthopedist, podiatrist, or any number of other medical practitioners concerned with foot conditions and disease. The user interface and other hardware and software of the scanning subsystem may be varied to suit the particular environment where it is located, whether office, hospital, retail, ambulatory center, or other suitable venue. The patient protective footwear referred to herein encompasses a custom shoe, a brace (such as a CAM walker), a boot, a cast, corrective footwear, an orthotic, an insole, or any other orthoses for treating the lower extremity.

Scanning subsystem 21 includes a scanner 22, such as a three-dimensional scanner for patient(s) lower extremities, or a similar device for detecting dimensions or other information related to the patient's lower extremities, gait, or other conditions under examination, or for otherwise receiving such inputs. The data generated by scanning subsystem 21 is further processed by a design engine, such as a podiatric design engine 23, which accounts for podiatric or other foot conditions. It will be appreciated that while design engine 23 is referred to as "podiatric," the system disclosed herein is not intended to be limited to podiatric professionals, but may likewise be suitable for many other medical practitioners who are called upon to provide individuals with suitable footwear to address foot conditions. As such, any practitioners dealing with conditions of the foot, regardless of title, specialty, or experience, may make use of this system, including the corresponding podiatric design engine 23, in order to have the design reflect the recommendations of such foot care practitioners.

In addition, the protection, accommodation, or other compensating features of the design may be generated at any number of points relative to the scanning process. In other words, the system may include suitable programming for the medical practitioner to input abnormalities or other data used to modify shoe and insole design and construction prior to the scan, to thereby create a suitable spreadsheet or other data structure accessible by the system in subsequent phases of operation. Furthermore, the digital scanning subsystem 21 itself may include suitable programming to detect abnormalities or other conditions requiring accommodation and either generate a default accommodation in subsequent design phases, or "flag" conditions for consideration through the user interface to the medical practitioner, so that design alterations can be considered. In still other implementations, suitable inputs related to the patient conditions which need to be accommodated can be received subsequent to the three-dimensional scan. For example, data input about foot conditions can likewise be received through the design engine 23, or any other suitable input means associated with either the scanner or other modules of the system.

Figure 4:
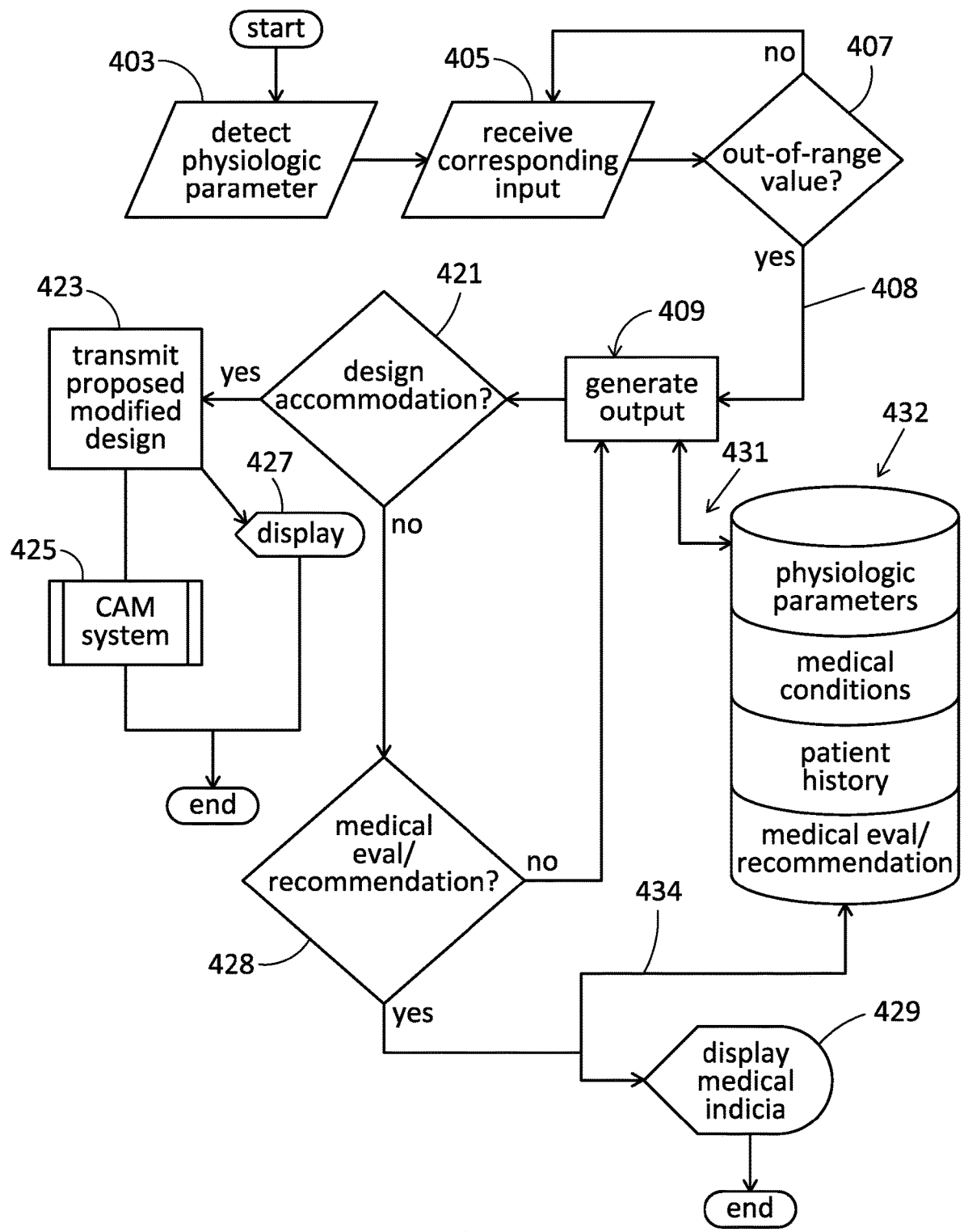
FIG. 4 is a flow-chart schematic of one possible computer-implemented operations, methods, and related programming of one aspect of the present disclosure.

Accordingly, in one possible implementation, another suitable way for system 19 to receive input may be through one or more sensors positionable relative to a lower extremity and adapted to detect one or more physiologic parameters of the lower extremity. In one method of evaluating protective patient footwear or the lower extremity, shown schematically in FIG. 4, the sensors could be configured or otherwise associated with programming so that, with regard to a lower extremity, the sensors are capable of detecting plantar pressure, friction, any other related forces, vectors or direction of such forces, temperature, contact area, acceleration, movement, moisture, temperature, and the timing of the foregoing parameters or elapsed time between sensing of certain magnitudes of the foregoing parameters (step 403). The above physiologic parameters could be gathered with reference to the lower extremity when the one or more sensors are positioned operatively to receive such parameters. For example, an array of sensors may be provided on protective patient footwear, stockingette, or other device for putting the sensors in operative proximity to the lower extremity. The one or more sensors may provide input to system 19 for evaluation, design or modification of protective patient footwear independent of, that is, without requiring, scanning subsystem 21, or the sensors may be combined with scanning inputs or still other data or inputs in other possible implementations.

The programming of modules of system 19 referred to herein may take the form of programmed or artificial intelligence, and such programming may be resident in design engine 23, as described herein, or in any other suitable modules associated with system 19. In one variation, design engine 23 or other suitable programming module is programmed to receive input from the one or more sensors corresponding to the physiologic parameter detected (step 405), and determine whether such input comprises an out-of-range value of the physiologic parameter (step 407). Thus, for example, system 19 may include, in its memory, data 432 corresponding to optimal or acceptable ranges of physiologic parameters associated with plantar pressure and the other enumerated parameters. Programming would, in turn, compare inputs received from the sensors against the optimal or allowable range of physiologic parameters and, in response to a determination that one of the inputs comprises a value out of the desired range of such physiologic parameter, the programming would generate an output to address such out-of-range value (step 409).

The output generated by the programming may comprise a design accommodation, such as a change to the geometry, material, or other design aspects as discussed in this disclosure (step 421). Among possible accommodations would be filling voids for missing tissue, addition of material to increase thickness at locations dictated by the location of sensor input, substitution of soft or harder materials, including friction-reducing material either on the vamp or other locations on an insole of the protective patient footwear or associated with a customized shoe, brace, boot, cast, or orthosis. The design accommodation may have specific dimensions associated with the proposed addition of materials, and may generate output in the form of design values for use in subsequent design, manufacture, or related dimensional modifications. Similarly, proposed geometry outputted by the system programming may take the form of dimensional changes or values for an insole or other aspects of the patient protective footwear.

The one or more design accommodations generated at step 421 can be suitably transmitted by system 19 (step 423), for example, in the form of an outputted design, to a computer aided manufacturing (CAM) system (step 425). An example of such CAM system is described subsequently herein with reference to module 27 and/or module 25. In addition, or alternately, design accommodation(s) may be displayed or outputted to other programming, or otherwise provided for subsequent use by medical practitioners, manufacturers or patients (step 427).

In another possible variation of system 19, the programming which generates output at step 409 may involve generation of outputs for use by a medical practitioner, as mentioned earlier in this disclosure. Such output may include suggested medical treatments, such as potential medical evaluations, which the practitioner may wish to consider performing on the patient, or one or more medical recommendations, which the practitioner may wish to convey to the patient (step 428). Medical recommendations may be generated in response to practitioner-provided inputs corresponding to patient exams, medical diagnostics or analysis, or in response to still other medical input provided to system 19, either at initial stages of patient evaluation or in response to detection of an out-of-range value in step 407. Medical evaluation and recommendation data outputted at step 428 may likewise be used in generating output in the form of design accommodations (step 421), such as by transmitting the fact of previous medical evaluations or quantitative data from such medical evaluations to be factored in the generation of output at step 409, such medical evaluation data, for example, being stored to memory (step 434) accessible to the programming that generates output at step 409.

Whether in the form of proposed evaluations for the medical practitioner to consider, or in the form of proposed treatment recommendations subsequent thereto, the output generated at step 409 may be transmitted so as to be suitably displayed or perceived by the medical practitioner or other end-user. Transmission and associated display may involve any of a wide variety of suitable electronic devices, including portable electronic devices, such mobile phones, personal digital assistant devices, tablets, laptops, computers, and the like, and may also involve having the output printed out or merged into other documents for further consultation (step 429). In such implementation, the generation of output at step 409 may access not only inputs corresponding to the physiologic parameters received at step 403, but patient history and medical conditions accessible to system 19 (step 431) through previous data storage (step 432) or contemporaneous input by the medical practitioner.

Figure 5:
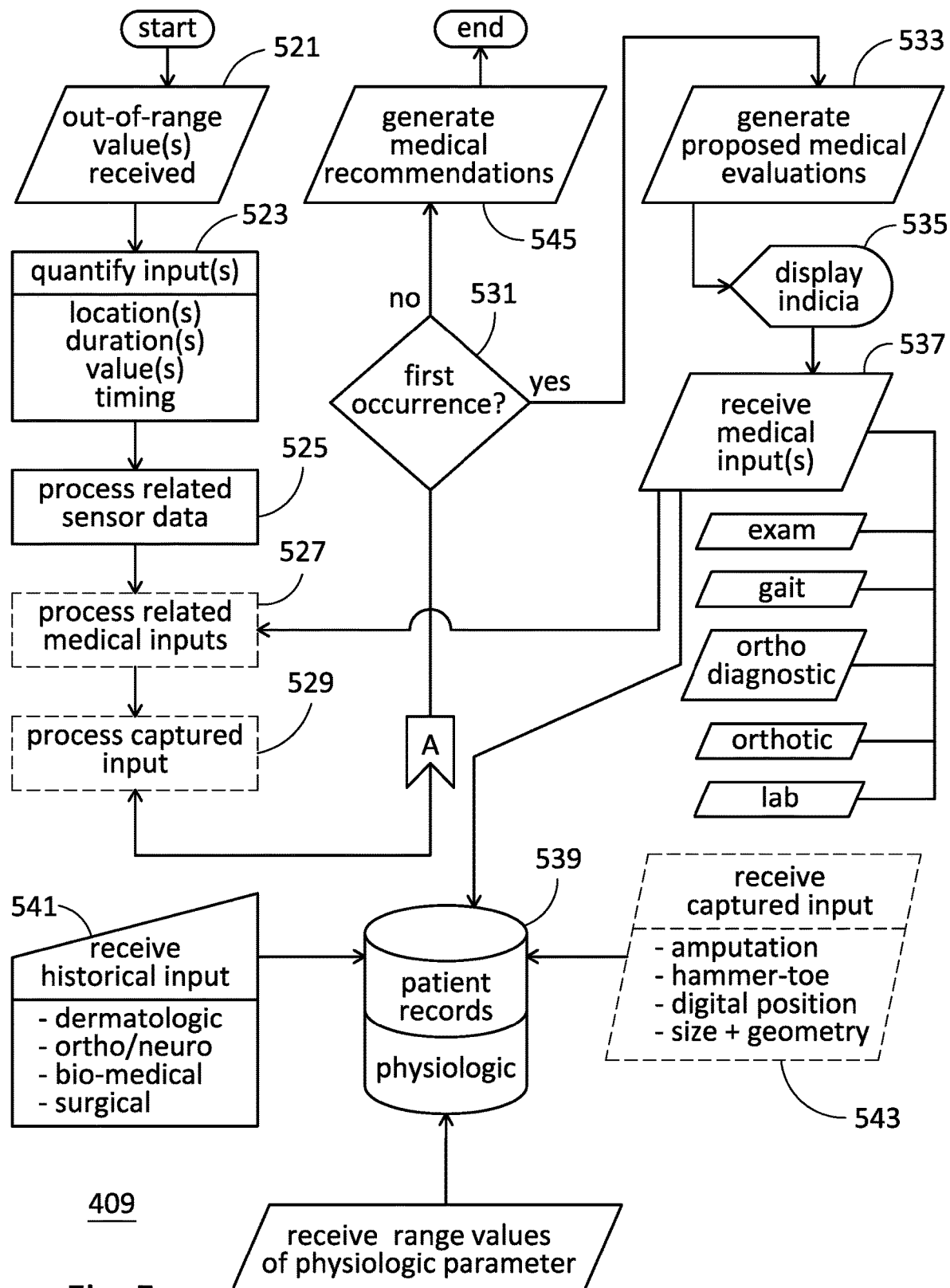
FIG. 5 is a flow-chart schematic of operations, methods, and related programming of another aspect of this disclosure.

One possible sequence of operations of system 19 to generate proposed medical evaluations and recommendations is discussed in more detail with reference to FIG. 5. Inputs are received and quantified and out-of-range values are determined or received at steps 521 and 523. Regardless of the exact order of the foregoing steps, after flagging certain sensor readings, that is, after determining that one or more values of inputs from the sensors are out-of-range, such flagged inputs are further quantified or processed by the programming associated with system 19. Thus, for example, upon detection of an out-of-range value, its location is determined, its magnitude beyond the acceptable range of the corresponding physiologic parameter is likewise determined, the duration of the out-of-range condition is calculated, as is the timing or periodicity of the out-of-range condition. So, for example, sensors of system 19 may be receiving physiologic parameters while the lower extremity is engaged in walking, and so the determination of out-of-range values may be part of a gait analysis or other dynamic evaluation. As such, timing of the out-of-range values in conjunction with location and magnitude may all become variables to be factored in by the programming (steps 523, 525).

The generation of outputs by program processes of system 19 may also factor in, that is, use as variables, physiologic parameters other than those associated with the out-of-range values, such as data inputs from other sensors, whether such inputs are within range or out-of-range. So, there may be foot conditions in which an out-of-range physiologic parameter on one portion of the foot is influenced by, or causally related to, a quantified input of another sensor. By way of example, an out-of-range pressure value under the first metatarsal of the foot may be evaluated by system 19 programming in relation to other inputs, such as a high moisture reading indicating a wound at that or another location, or a lack of pressure at other plantar areas causing pressure to concentrate on the aforementioned first metatarsal, or other potentially related physiologic conditions detected both at the first metatarsal and at other areas of the lower extremity, as detected by one or more sensors of a suitable sensor array (step 525).

System 19 may generate output of medical recommendations and medical evaluations not only by quantifying inputs from sensors, including out-of-range values received, but also by factoring in, that is, using as variables, other related medical inputs (step 527) or scanner input (step 529). In one possible variation, when data available for the patient under evaluation does not include certain medical information, system 19 may generate one or more outputs corresponding to a first occurrence of the out-of-range value (step 531). One or more such outputs may be selected from a set of treatment or evaluation recommendations. Suitable programming of system 19 may thus generate output in the form of proposed medical evaluations (step 533) and display associated indicia (step 535) on a suitable interface accessible to the medical practitioner. Medical evaluation indicia generated by system 19 as output could include the notification of the medical practitioner's office or the medical practitioner to contact the user whose lower extremity is under evaluation and schedule an appointment. Programming could recommend a quantified timeframe for such contact factoring in the extent that quantified inputs are out-of-range. Still further, depending on the inputs which are received, quantified, and processed in accordance with the programming in steps 523, 525, and 527, proposed medical evaluations may include, without limitation, a medical examination of the patient or the lower extremity (or both), a gait evaluation, dermatologic or orthopedic diagnostic procedures, an evaluation of the insole or other protective patient footwear, advanced testing, such as X-rays, MRI, blood flow, ultrasound, and the like, as well as lab work to identify the presence of infection, elevated blood sugar, inflammation, or other metabolic disorders.

During operation of system 19 to generate output for use by medical practitioners, programming is available so as to receive medical inputs from any of the foregoing tests, exams, evaluations, and the like (step 537). Such medical inputs can be suitably stored as patient records of a suitable database or data file 539 or other suitable memory. It should be noted that patient records may include input of historical information dating from previous examinations, whether dermatologic, orthopedic/neurological, bio-mechanical, or surgical (step 541). Likewise, data files and patient records associated with database 539 may have therein either concurrently generated or historical scanner input indicating lower extremity conditions such as amputation, hammer-toe, digital position, and size and geometry of physiologic, orthopedic, and other lower extremity characteristics (step 543).

In addition to generating output in the form of proposed medical evaluations in step 533, system 19 is suitably programmed to generate further output corresponding to one or more medical recommendations (step 545). The further output of medical recommendations may involve programming to select indicia from another set of treatment recommendations, such further set reflecting the fact that the lower extremity under evaluation (and its corresponding protective patient footwear) has been a subject of previous out-of-range readings, recent medical inputs corresponding to exams, gait analysis, or other medical evaluations previously proposed at step 533. As such, programming generating medical recommendations at step 545 uses previous occurrences of out-of-range values and recent medical condition inputs as variables or factors in generating corresponding output of medical recommendations. Medical recommendations generated may be communicated to the medical practitioner through suitable indicia appearing on a suitable interface, and may include behavior modification, such as decreasing activity, decreasing time of walking, decreasing time of standing; increased use of certain insoles, orthotics, or offloading devices of other types of protective patient footwear, either periodically or permanently; increased use of assistive devices like canes, walkers, rollers, or wheelchairs; the control of metabolic, such as blood-sugar levels, caloric intake, and weight loss recommendations; lifestyle factor control recommendations, such as increase of physical activity, cessation of smoking, reduction of alcohol consumption, modification to diet, reduction of stress, and improvement of sleep and any other medical recommendations related to out-of-values or other inputs to system 19.

Medical recommendations generated at step 545 may include one or more modifications to protective patient footwear, such as an insole, being used by the patient; a recommendation for a different device to lessen the out-of-range value received. Such recommendations may factor in medical inputs received in steps 537, 541 and comprise indicia directed at decreasing the risk of lower extremity injury or lower extremity trauma leading to a reoccurrence of out-of-range values previously detected. Generated recommendations may comprise indicia for physical therapy; for muscular, proprioceptive and gait training; consultation with orthotic or prosthetic professionals; recommendations regarding neurology, psychiatry, orthopedic, and other medical practitioners relating to treatment of gait disturbance; or potential surgical corrections. Medical recommendations generated by programming of system 19 may likewise be tied to protective patient footwear under evaluation itself and related out-of-range values received, such as repairing or replacing the protective patient footwear; modifying it in terms of geometry or material to address the out-of-range value(s) received; replacing worn-out materials; or changing materials to address friction, inflammation, and other lower extremity conditions.

Likewise, the medical recommendations generated at step 545 may propose diagnostic procedures not normally considered in addressing a first occurrence of an out-of-range value or in an early phase of difficulties as done when medical evaluations are generated in step 533. Thus, step 545 may generate output selected from a set of indicia corresponding to more advanced testing, such as vascular studies, $O_2$ profusions, biopsy, and the like.

The generation of output by system 19 corresponding to medical recommendations 545 may be accomplished by programming which factors in, such as by using as variables, the presence, absence, or magnitude of medical inputs received in step 537, out-of-range values received in step 521, the quantification of such inputs accomplished in step 523, the relation of such inputs to one or more other sensor values in step 525, and processing of medical inputs 537 in step 527, as well as the potential for historical input applicable to the out-of-range value under evaluation (step 541), and scanner input contemporaneously or previously received in step 543. One or more of the foregoing inputs and related values thereof may be selectively used as variables or factors by the programming in generation of outputs relating to medical evaluations (step 533) or medical recommendations (step 545).

Figure 6:
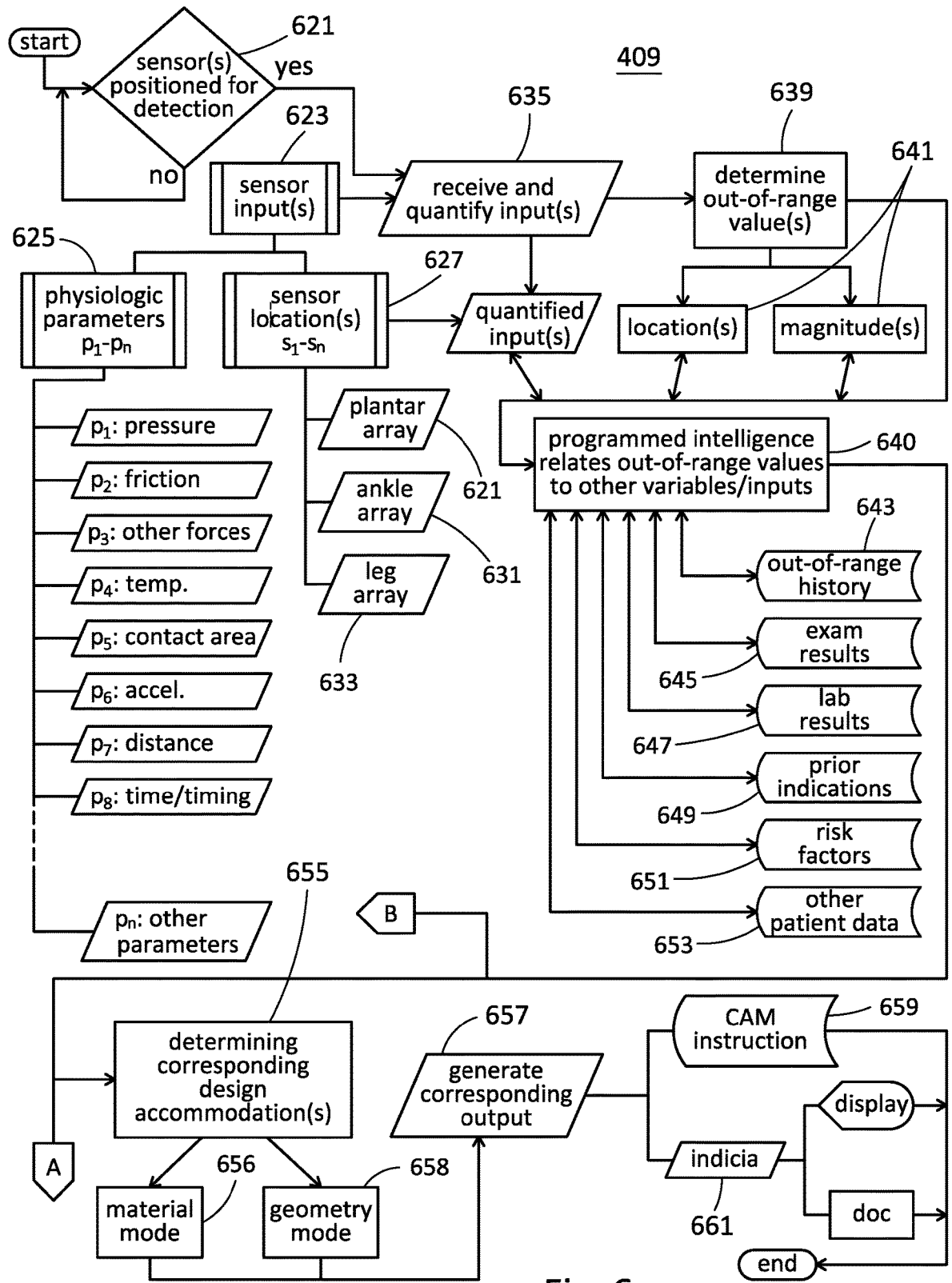
FIG. 6 is a flow-chart schematic of operations, methods, and related programming for still another aspect of this disclosure.

Referring now to FIG. 6, the programming of system 19 related to generating output (step 409) in the form of one or more design accommodations (step 421) will now be discussed in more detail with reference to one possible method of operation. System 19 awaits confirmation that sensors have been positioned in operative proximity to a lower extremity and/or associated protective patient footwear for evaluation (step 621). If so, system 19 receives sensor inputs 623, which may encompass any of the physiologic parameters 625, labeled $p_1$ through $p_n$, and identified herein and in FIG. 6, from one or more sensor locations 627, labeled $s_1$-$s_n$. Sensor locations 627 may comprise any suitable array associated with the lower extremity, whether a plantar array 629, an ankle array 631, or a leg array 633, or all or any combination of the foregoing. Inputs are received and associated with a value or otherwise quantified at step 635, and suitably stored in a data file, memory, or other data structure 637.

After sensor inputs 623 from sensor locations 627 are evaluated to determine out-of-range values (step 639), corresponding locations and values/magnitudes are suitably stored in memory or other data structures 641. At step 640, one or more out-of-range values determined in step 639 may be related by programming of system 19 to other sensor inputs, variables, and medical inputs to determine design accommodations (step 655), such medical inputs including patient history of out-of-range values 643, prior indications associated with the patient and lower extremity under evaluation 649, risk factors 651, and other patient data 653.

The design accommodation may include any number of modifications to the protective patient footwear under consideration, whether in the form of an orthotic, CAM walker, boot, brace, cast, shoe, or any other orthosis for treating the lower extremity, such as addition or substitution of materials and geometric modifications to any of the foregoing. The output generated for the design accommodations (step 657) may be in the form of suitable instructions for computer-aided manufacture (CAM) systems (step 659) or suitable indicia either displayed (661), prepared as a document, or otherwise communicated to parties involved in addressing the out-of-range value(s) with suitable design accommodation(s).

As one example of generating design accommodations in response to receiving one or more out-of-range values from one or more sensors, system 19 and its associated programming may be used in evaluating protective patient footwear, whether it be an insole, CAM walker, brace, boot, cast, or other orthosis, for a diabetic with a current ulcer or at risk thereof. One of the sensors in operative proximity to the first metatarsal of the right foot may identify the physiologic parameter $p_1$, corresponding to an out-of-range pressure (in this case, high pressure) against the plantar surface of such first metatarsal. The high pressure may trigger a flag or otherwise generate an alarm condition and not thereafter be subject to further quantifying. In such binary implementation, in response to the out-of-range value, programming generates an output that provides the medical practitioner with options to address the out-of-range value at the level of recommending a change to gait, recommending the addition of an assistive device like a walker or crutches, or recommending consideration of insole or orthotic modifications, including a change of geometry or material. In one variation, the implementation above may be adapted for use by the patient including generated output suitable for such patient. Such output may likewise be suitable for additional medical professionals involved in recommending orthoses or medical professionals other than a primary caregiver, podiatrist or orthopedist.

Furthermore, the programming of system 19 responding to the out-of-range value of high pressure under the first metatarsal may make more granular outputs by not only further quantifying the out-of-range value associated with the first metatarsal, but relating it to: levels or tiers of physiologic parameters stored in a suitable database, the presence of out-of-range values in other parts of the lower extremity, and the values of sensor data even if not out-of-range, as well as medical inputs concurrently or previously received relating to conditions of the lower extremity provided by exam, diagnostic tests, lab results, or medical history, as discussed previously with reference to FIGS. 4-6. In such cases, programming may not only generate treatment recommendations for patient, practitioner, or other professional, but may generate quantified accommodations to the design of protective patient footwear or modification to existing protective patient footwear.

In one variation, the generation of output (step 409, FIG. 4) includes not only the generation of design accommodations diagrammed in FIG. 6, but alternatively or in addition, may also include call routines, program options, or logical branches to invoke the generation of medical evaluations and medical recommendations discussed previously. Such option is shown by process link A in FIG. 6, which branches to corresponding process link A in FIG. 5 associated with generation of proposed medical evaluations (step 533) and medical recommendations (step 545).

Figure 7:
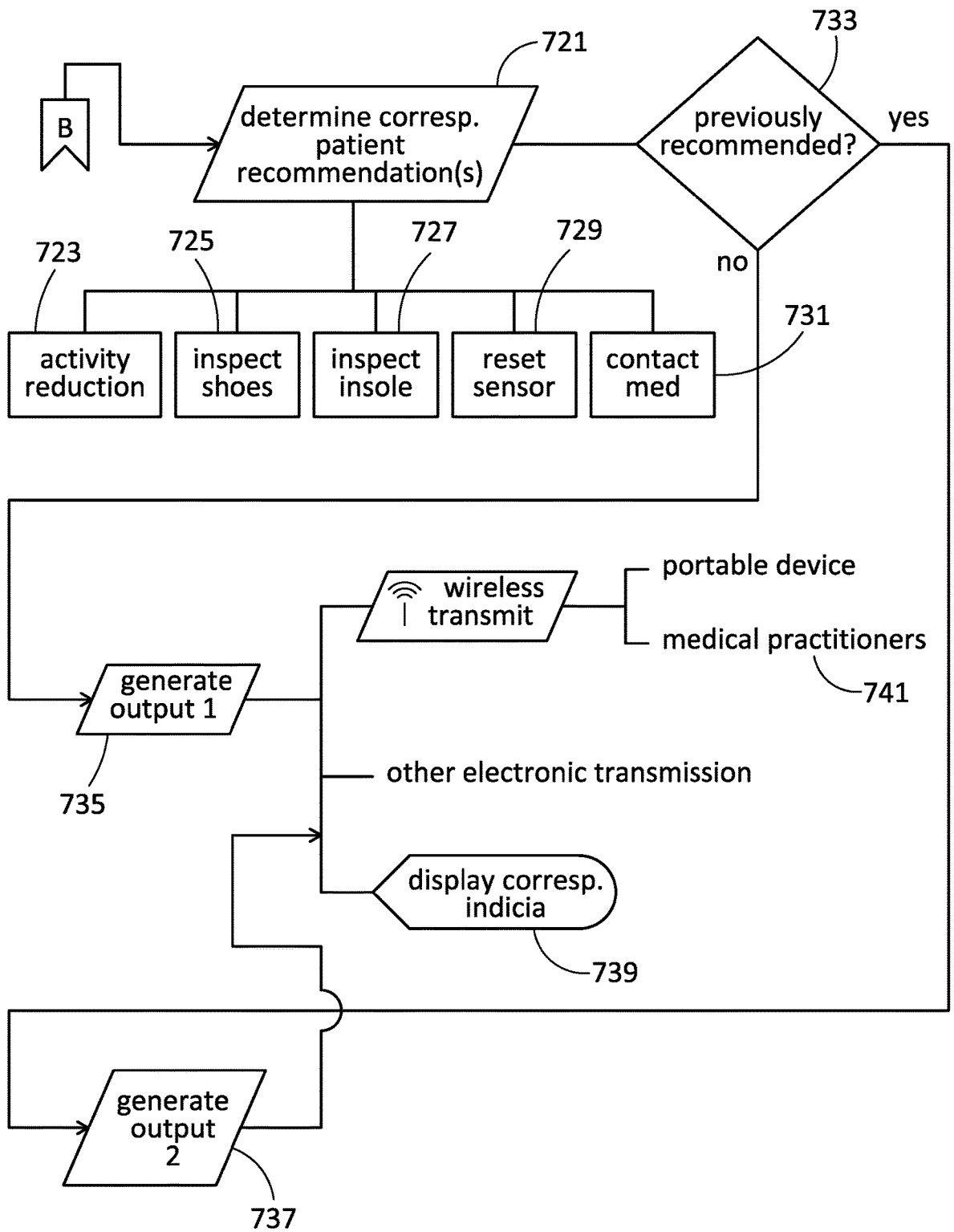
FIG. 7 is a flow-chart schematic of operations, methods, and related programming for a still further aspect of this disclosure.

In still another variation, the processing of out-of-range values in connection with the variables and inputs outlined with reference to FIG. 6 may be used in conjunction with a patient- or user-oriented implementation of system 19, as shown schematically in FIG. 7. After suitable processing of out-of-range values at step 640 in FIG. 6, program branch labeled B makes use of suitable programming to determine patient recommendations appropriate for the out-of-range values as a function of the other variables and inputs (step 721). Programming of system 19 may select one or more patient recommendations from a set of patient indicia in the process of generating output, such as activity reduction; insole, shoe, or other protective patient footwear inspection; resetting of the sensor, or indicia to contact of a suitable medical practitioner (723, 725, 727, 729, 731, collectively) within a time-frame determined by programming upon factoring in the aforementioned inputs.

The patient-oriented module determines whether a previous one or more of the physiologic parameters being sensed has been the subject of an out-of-range value previously and differentiates the generation of output as a function of such previous occurrence (step 733). In the event that the patient has not previously received one of the recommendations, or not previously had a certain one or more of the out-of-range values detected, then a first range of possible outputs is generated (step 735). Such output may involve wireless transmission, such as to a wearable computerized fitness device, mobile phone, or other portable device, either in possession of the user or another associated party. Such outputs may include the display or communication of indicia to contact a primary care or specialist medical professional, or another professional potentially tied to orthoses associated with out-of-range values. Patient recommendations generated may likewise include admonitions or indicia associated with reducing walking by volume or distance, increasing rest by corresponding amounts, elevating the lower extremity, the foregoing outputs including timeframes and other quantified aspects for reductions based on the magnitude of the out-of-range value detected, or other factors processed by the programming to indicate severity or lack thereof.

Likewise, a patient recommendation to inspect footwear associated with the lower extremity, insoles, or other orthoses may be among the set of outputs generated at step 735, along with replacing broken or worn insoles, and resetting the sensor or otherwise confirming its satisfactory operation. Output generated at step 735 may also be electronically transmitted to a suitable patient-maintained or professionally-maintained database, and corresponding indicia may be displayed visually or audibly, depending on the application.

In the case of a repeated, out-of-range value or other repeated condition, or in the case of repeating a previous patient recommendation, programming of the patient module may generate one or more outputs which are differentiated from the outputs previously discussed, as in the case when the repeated out-of-range value or repeated recommendation may require more immediate attention or more extreme intervention. In such cases, audible alarms or automatic emergency transmissions may be generated, or indicia may be generated for auditory or visual perception by the patients, such as indicia warning to immediately cease activity and contact a medical professional within an immediate or other timeframe calculated as a function of the severity of the out-of-range value or the extent of repetition of the recommendation, (step 737).

The modules associated with receiving sensor input, determining one or more out-of-range values for such sensors, and generating corresponding output, whether a design accommodation, medical evaluation/recommendation, patient recommendation, or any or all of the foregoing, may be associated with design engine 23, as certain of the outputs generated by the programming relate to either evaluation of a lower extremity to be treated with protective patient footwear, or the evaluation, design, or modification of protective patient footwear. In addition, such functionality and associated programming may be in modules within design engine 23, even for purposes of generating medical evaluation output or medical recommendation output, or in modules separate from design engine 23.

Patient oriented system 19 may be stand-alone or likewise included within design engine 23 or other modules of the system. Still further architectural constructs for the programming described with reference to receiving and processing sensor input are within the scope of the present disclosure, whether within design engine 23 or other modules of system 19.

The receiving of inputs and the related processing, as described throughout this disclosure, may involve serial processing, parallel processing, or both, or any other suitable computer-implemented steps, data calls, instruction execution depending on the implementation. In addition, when this disclosure describes factoring in inputs or using them as variables, those terms are to be interpreted in their broadest sense in the computer arts, including, without limitation, not only numeric calculations, but yes/no determinations, if-then/else-do, compares, occurrence/non-occurrence, conditional operations, relational database operations, look-ups, and the like, as appropriate for the functions described, including the various outputs generated by system 19.

Regardless of when the patient particulars are received by system 19, system 19 can include suitable programming to automatically alter certain corresponding aspects of the protective patient footwear design, or present suggested alterations to the medical practitioner through a suitable graphical user interface. In one version of the system, design engine 23 may be configured to include suitable software programming to allow for the accommodation of any number of dermatologic, orthopedic, neurologic, biomechanical, and surgical conditions in the resulting footwear design. Modification of such design and the corresponding custom construction therefore can address findings of the medical history input into the system, as well as parameters relating to the scanning or other physical exam findings. Dermatological parameters such as wounds, calluses, fissures, high pressure areas, at-risk areas, fat pad atrophy, tissue loss, excess tissue, and scars may be the subject of suitable programming, so that upon detection of, or input related to, these conditions, modifications to the corresponding design, virtual last or ultimately the footwear to be fabricated are incorporated into the operations of system 19. Similarly, orthopedic or neurological conditions may be the subject of suitable programming in the system, including neural functions and muscle functions, particular positions of hips, knees, ankles, and the subtalar joint. Range of motion of hips, knees, ankles, and subtalar joints, as well as the range of motion of greater and lesser metatarsophalangeal joints, proximal and distal inter-phalangeal joints—any or all such conditions may be received as input into the system through suitable programming, and may be factored into design recommendations or the ultimate design of the particularized footwear. Still further, foot position and geometry, whether related to the ankle, rear foot, mid-foot, forefoot, or digits may be scanned, input, or otherwise reflected in the operation of design subsystem 23.

The system may also include suitable programming to allow for accommodation of surgical conditions. For example, surgeries related to the hips, knees, ankles, tendons, amputations, thigh, tibia, fibula, related joints, and of course, the foot, as well as vascular or other effects of such surgeries, such as arterial bypass, vein surgery, or stents, on the proposed footwear-any or all may be inputted or detected by suitable programming in design subsystem 23.

It will be appreciated that any number of additional factors may be the subject of suitable programming, hardware, or peripherals in the design subsystem, such that corresponding accommodations, as judged appropriate or suitable, may be made to the design and resulting footwear. So, as an example, system 19 may include additional hardware to analyze biomechanical factors, such as motion detectors, accelerometers, or any number of sensors, along with corresponding programming, adapted to provide suitable data for use in the footwear design.

System 19 may include suitable programming to accommodate a prior amputation of the great toe, as just one example of the sorts of conditions which can be accommodated. One possible approach would be for system 19 to receive either prior to scanning, during scanning or otherwise input data specific to the level of amputation involved, as well as the effect of the amputation on foot function, the dermatological condition of the amputation site, and a biomechanical evaluation and gait analysis. These latter two factors may either be detected by suitable motion detectors associated with the system or input through a suitable user interface by the medical practitioners (or both), and suitable programming will be devised in response to such inputs to reflect the missing tissue or functional alterations in the corresponding design. Among possible accommodations which the system can be programmed to make would be the addition of insole materials to fill voids for the missing tissue. Such operations could be contemplated in three dimensions at the design stage and in the corresponding manufacturing stage discussed subsequently. The system programming may have a default or various suggestions for filling the void based on information collected.

Another possible accommodation from such amputation would be the addition of materials under the remaining portions of the foot to account for additional pressure and forces that are transferred due to the amputation. Again, suitable programming can either respond to the detection of the amputation or the input of information corresponding to such amputation, and alter the scanned data accordingly or alter any of the other information used to determine the amount of material under the foot. System programming may likewise suggest a default to the addition of material to the insole to protect the residual portion of the first metatarsal from increased or abnormal forces.

In response to the detection of, or input related to, gait abnormality, suitable programming may alter scanned data or otherwise result in the provision of materials both in the insole and in the ultimate shoe construction. For example, in such situations, the medial portion of the insole underlying the filler for the missing digit could be stiffened with a harder or mixed density material. Different types of material might also be suggested by the system in response to detection or input of a gait abnormality, so as to transfer weight and achieve better balance across a patient's remaining foot surface. Programming may also modify or suggest modification to the insole and outsole of the shoe to accommodate for abnormal forces from such amputations.

Still further, the mechanical characteristics of the midsoles and outsoles themselves may be modified by the system programming in response to data received relating to gait abnormality of the prior amputation. Such modification would increase the flexibility in the area of the metatarsal-phalangeal joints, so as not to increase the forces or weight bearing load on the remaining function of the foot.

The system may be suitably programmed to not only alter scanned data or the associated design in response to foot conditions, but to do so in a manner that does not alter the external appearance of the shoe from that "normally" expected—in other words, so that to the outside observer, there is no aesthetic indicator of the underlying deformity or modifications.

The system may also be programmed to accommodate into design and manufacture a prior history of ulceration or a wound in the plantar surface of the second metatarsal-phalangeal joint. One approach would be to allow the medical practitioner to input historical information related to ulceration or wounds in a series of interrelated fields in a suitable user interface. As such, the system is programmed to identify and detail the etiology and location of the prior wound or ulceration. For such conditions, the system may likewise have suitable input programming so that foot function is recorded through suitable input, dermatological conditions and scarring assessed, biomechanical and gait evaluations inputted, and other input relating to abnormalities or factors that either caused, or resulted from, the prior wound or ulceration. The system is programmed to quantitatively evaluate the nature and character of the inputs and thus use them as variables to alter the data or design arising from digital scanning, such alterations potentially accommodating the missing tissue, changes to the skin, and other functional alterations. Another possible approach to the situation of prior ulcerations and wounds would be for the system to be programmed to modify insole materials to accommodate missing tissue, loss of elasticity, or lack of impact absorption due to scarring and tissue loss.

The accommodation of ulceration and wounds to the plantar surface may also be programmed to suggest specific insole top cover materials to aid in friction reduction to the area at risk. Similarly, the shape and dimensions of the insole may be modified in response to wound data received in order to protect the prior wound site and the remainder of the foot.

The programming of the system may permit modifications to be done in three dimensions, using the factors relating to the prior history of ulceration and wounds, along with information collected from the scan. Again, the exact sequence of scanning, detection of, or inputs related to conditions requiring accommodation can be varied. For example, proposed or suggested accommodations may be input prior to scanning and factored into the subsequent scan, or the scanning may proceed first, with the resulting design receiving modifications or suggested modifications as a result of the detected or inputted abnormalities.

Programming may also be devised to alter material type and thickness in response to receiving input indicating a particular cause of the wound. Similar to the previous discussion on great toe amputation, the style, shape, and materials of the midsole may be revised to offload the previously wounded area and protect the remainder of the foot. In response to suitable wound or ulceration input, the system may suggest or automatically alter outsole material, including its design and functionality, so as to address the mechanics of the foot and protect from reinjury of the wound or ulceration.

As another example of customizing footwear to address foot conditions, the system may include suitable programming to accommodate an osseous deformity of the toes, so-called "hammer toes." In relation to scanning of the foot, as described in the previous examples, suitable programming will permit the detection or receipt of input of data related to digital position, associated muscle function, and gait analysis. The system may likewise allow foot function to be characterized with suitable inputs for subsequent processing, as well as dermatologic conditions of the toes, and the condition of the plantar skin—any or all such factors being suitably processed by the system, for example, by the design engine 21, in order to accommodate for the deformity. In the context of hammer toes, the system may include specific programming so that the size and shape of the forefoot noted from the scanned image is factored into the overall design. The noted forefoot dimensions may thus be processed by the system (i.e., the design engine 23), to automatically recommend or select particular materials for the top cover and vamp of the shoe to be manufactured, such materials selected for their properties to protect and provide space for the hammer toe deformity.

Similar programming of this system can accommodate the hammer toe deformity by automatically adjusting or making suggestions to adjust size, material, and shape of the insole as a function of the support, protection, and accommodation needed for digital contraction and changes to the associated dorsal and plantar skin. To the extent the hammer toe deformity causes mechanical and gait abnormalities, design engine 23 in particular, or the system in general, may be suitably configured to modify or suggest modifications to outsole design and shape, including increased flexibility, roller-rocker construction, fillers and pads, the use of shear reducing materials, friction reducing liners, and heat adaptable materials. As with the previous accommodations discussed, suitable programming to address the hammer toe deformity will allow for accommodations while maintaining the external appearance of the shoe, so that to the outside observer, there would be no aesthetic indicator of the underlying deformity.

As seen by the above examples and description, design engine 23 and the overall system 19 for designing and manufacturing protective patient footwear include a rich set of tools, features, and associated programming so that the many variables and possible accommodations to protect or accommodate a patient's foot condition can be efficiently orchestrated into a customized and suitable design to achieve therapeutic ends.

It would be appreciated that the interface through which foot conditions are input into the system may be varied to suit any number of applications. Checklists, menu-driven screens, and any number of automatic detection and scanning methodologies may be used to provide data associated with the patient's condition and the optimal or available design alternatives to address such conditions. The disclosed system has been programmed to suit the particular needs of foot specialists so as to design and manufacture the resulting protective footwear in a more straightforward fashion.

Having discussed the scanning subsystem 21 and design engine 23, and the various programming for generating associated footwear designs associated with the system and design engine 23, the present system 19 also may integrate computer-assisted manufacturing operations. So, for example, in the implementation illustrated in FIG. 1, a virtual last creation subsystem 25 may be included in system 19. The phrase "virtual last" is meant to refer to the electronic representation of a three-dimensional last used in connection with the making of corresponding footwear. In one implementation, the virtual last represents a typical "male" structure, and is used in subsequent automated manufacturing to correspond to the interior of the customized shoe, with materials being built to the outside of such last. Any number of other forms of virtual lasts are also contemplated, including a "female" mold inside of which would be built or manufactured the associated customized shoe. A combination of male and female molds may likewise be used either in conjunction with an injection molding process or as an intermediary to generate the required jigs or other forms associated with injection molding processes. In one implementation, virtual last creation subsystem 25 functions to perform computer-aided design and computer-aided manufacturing.

In still other implementations, it will be appreciated that virtual last creation subsystem 25 is optional, and that design engine 23 may programmed to generate the protective footwear design from suitable processing of the data received from the scanning subsystem 21. Still other arrangements of design functionality in one or more subsystems are possible, depending on the particular implementation.

In one implementation, the use of injection molding is such that the insole is integrated into the shoe, as opposed to being a separate piece which is fitted inside the footwear and thus prone to slippage or loss.

The exact exchange and formatting of data received by system 19, from the scanning of the foot to the generation of the virtual last, may occur with or without design engine 23. Depending on the implementation, manufacturing-ready output may be generated in the virtual last creation subsystem 25, the design subsystem 23, or even as early as the scanning subsystem 21. In other words, depending on the particular application, the data necessary to create the virtual last may be generated at any number of phases in the described system, whether it be scanning, design, or last creation.

The above-described system may include suitable computer-aided manufacturing functionality so that the virtual last may be used to fabricate the customized shoe as an end product. In one possible implementation, suitable output files are generated by one or more of the preceding subsystems 21, 23, or 25 of system 19 so that an injection molding process may be used to create the customized footwear. The use of injection molding may be used exclusively or in combination with other techniques. Such injection molding may be accomplished by manufacturing subsystem 27 shown schematically in FIG. 1.

Figure 2:
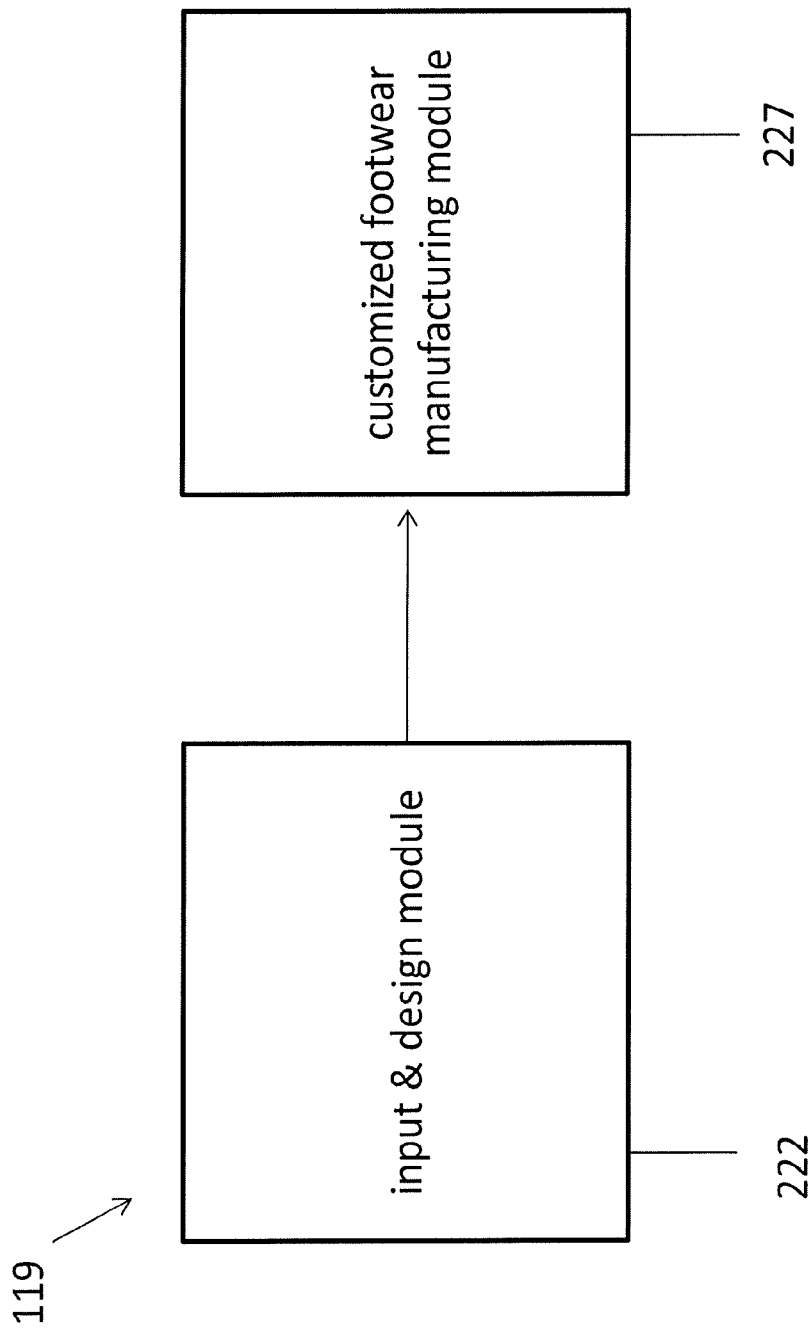
FIG. 2 is a schematic of another possible implementation of the present disclosure.
Figure 3:
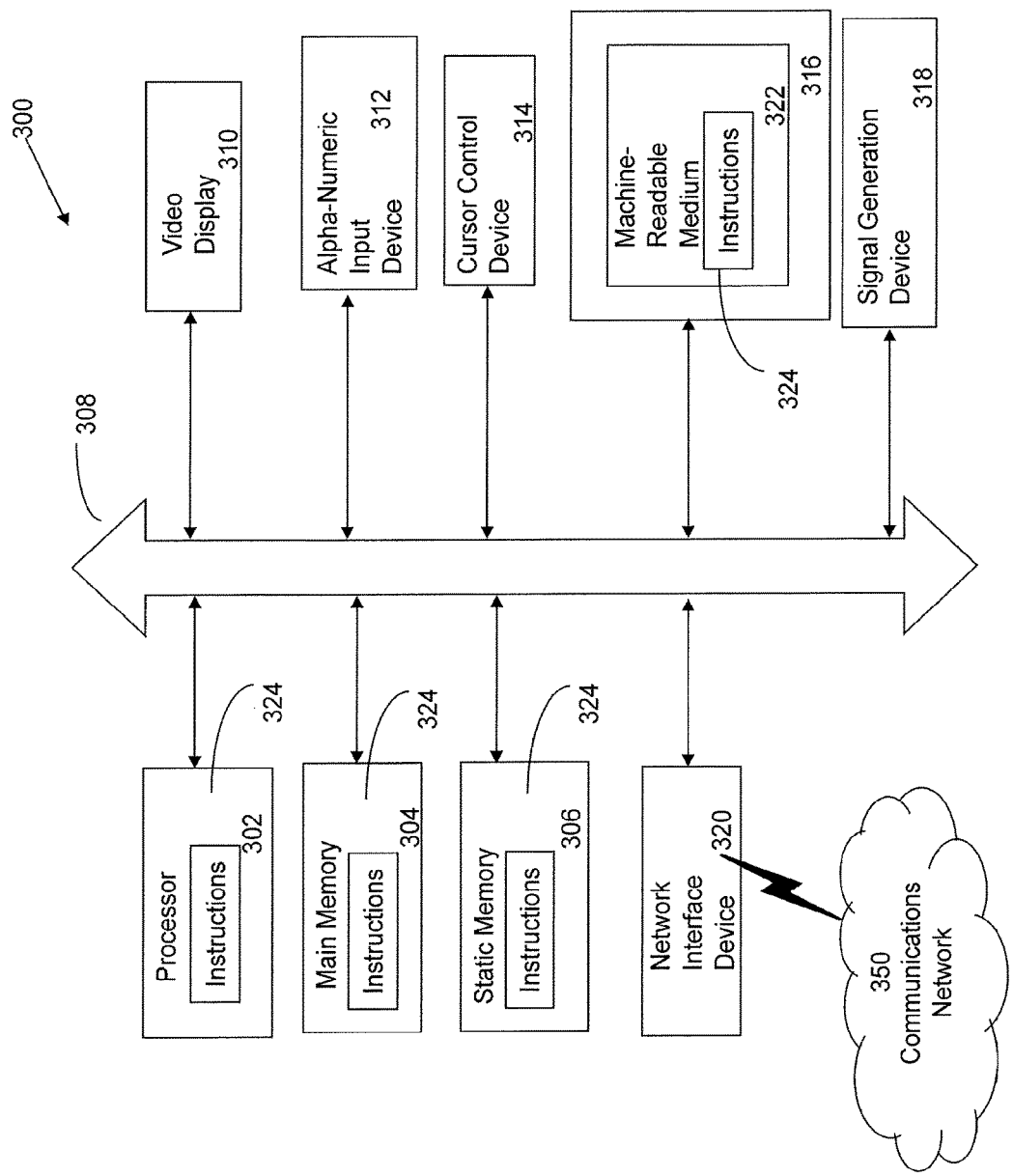
FIG. 3 is a schematic of one possible computer implementation of the present disclosure.

The exact dividing line between scanning subsystem 21, design subsystem or engine 23, virtual last creation subsystem or module 25, and the manufacturing subsystem 27 may vary depending on the particular application. It is also possible that functionality from one subsystem may be integrated into others such that one or more of the four subsystems discussed above are eliminated. So, as an example, in another possible implementation shown schematically in FIG. 2, system 219 can be configured to include an input and design module 222 corresponding to all or part of the functions performed by scanning subsystem 21 and design engine 23 of one of the previously described implementations. A customized footwear manufacturing module 227 is adapted to receive suitable output from module 222 to create the requisite footwear, similar to the functions described in manufacturing subsystem 27 of the previous implementation. The intermediary of a virtual last may or may not be applicable to such systems.

Certain quality and design checks can be included in the above-described system, to ensure that the suggested accommodations are appropriate in the resulting product and meet the patients' needs. It is likewise possible that any one of the modules can be the subject of multiple iterations, as different options are tried and different prototypes are created.

The operation of the systems disclosed herein makes use of suitable input devices, whether scanners, cameras, x-ray or other medical imaging systems, pressure plates, keyboards, and the like.

System 19 may be implemented on any suitable computer platform, using either stand-alone or networked architecture. In one version, there may be one or more Lower extremity-specialist scanning stations in communication with a database or other data storage means, one or more servers or processors, either through a local-area or wide-area network. A client-server architecture using the world-wide web may also be used. In the event computer work-stations are involved, whether as stand-alone versions of system 19 or as just housing foot-specialist input subsystems, such workstations may comprise a computer system 300 which includes a processor 302 (e.g., a central processing unit (CPU), a graphics processing unit (GPU, or both), a main memory 34 and a static memory 306, which communicate with each other via a bus 308. The computer system 300 may further include a video display unit 310 (e.g., a liquid crystal display (LCD), a flat panel, a solid state display, or a cathode ray tube (CRT)). The computer system 300 may include an input device 312 (e.g., a keyboard), a cursor control device 314 (e.g., a mouse), a disk drive unit 316, a signal generation device 318 (e.g., a speaker or remote control) and a network interface device 320.

The disk drive unit 316 may include a machine-readable medium 322 on which is stored one or more sets of instructions 324 (e.g., software) embodying any one or more of the methodologies or functions described herein, including those methods illustrated above. The instructions 324 may also reside, completely or at least partially, within the main memory 304, the static memory 306, or within the processor 302, or a combination thereof, during execution thereof by the computer system 300. The main memory 304 and the processor 302 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs in the broad sense to include, without limitation, computer coding, microcode, firmware, or other programing, such software running on a computer processor or other microprocessor. Furthermore, software implementations can include distributed processing or component/object distributed processing, parallel processing, or virtual machine processing can also be constructed to implement the methods described herein. The instructions 324 may further be transmitted or received over the communications network 350 via the network interface device 320.

While the machine-readable medium 322 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Accordingly, the specification and drawings are to be regarded in an illustrative rather than a restrictive sense.

The foregoing is provided for purposes of illustrating, explaining, and describing embodiments of this invention. Thus, although specific arrangements have been illustrated and described herein, it should be appreciated that any arrangement calculated to achieve the same purpose may be substituted for the specific arrangement shown. Combinations of the above arrangements, and other arrangements not specifically described herein, will be apparent to those of skill in the art upon reviewing the above description. Therefore, it is intended that the disclosure not be limited to the particular arrangement(s) disclosed herein.

What is claimed is:

1. A computerized system for evaluation of protective patient footwear for a lower extremity, the system comprising:
   a design engine implemented on a computer having programmable memory and at least one processor that executes instructions stored in the programmable memory;
   at least one sensor positionable relative to the lower extremity to detect at least one physiologic parameter of the lower extremity, the physiologic parameter selected from the group consisting of plantar pressure, friction, temperature, force, force direction, contact area, acceleration, movement, moisture, temperature, and elapsed time;
   wherein the design engine is programmed to (a) receive input from the sensor corresponding to the physiologic parameter detected; (b) determine whether the input comprises an out-of-range value for the physiologic parameter; and (c) in response to the determination, generate an output to address the out-of-range value, the output consisting of at least one of a design accommodation and a treatment recommendation;
   wherein the design accommodation, when generated, corresponds to at least one of a proposed geometry and a proposed material of the protective patient footwear, and wherein the design accommodation is selected from a set of the design accommodations pre-programmed to correspond to the physiologic parameter for which the out-of-range value was detected;
   wherein the design accommodations comprise an addition of insole material to fill voids from an amputation, a modification of materials under unamputated lower extremity portions to relieve lower extremity-related forces due to the amputation, inclusion of at least one of stiffer materials and more flexible materials relative to surrounding material of the protective patient footwear to address a gait abnormality related to the amputation.

2. The system of claim 1,
   wherein the sensor is positionable at a location on the protective patient footwear to detect the physiologic parameter of plantar pressure on the first metatarsophalangeal joint when the lower extremity is associated with the protective patient footwear; and
   wherein the design engine is programmed to determine whether the input from the sensor comprises an out-of-range value of the plantar pressure at the first metatarsophalangeal joint.

3. The system of claim 1, further comprising a patient interface, a plurality of the treatment recommendations, and first and second patient programming, the first patient programming adapted to transmit patient indicia corresponding to the treatment recommendation to the patient interface, the indicia comprising at least one patient recommendation selected from a first set of indicia of the patient recommendations.

4. The system of claim 1, further comprising a medical practitioner interface, a plurality of the treatment recommendations, and medical practitioner programming adapted to transmit medical practitioner indicia corresponding to the treatment recommendation to the medical practitioner interface, the medical practitioner programming capable of determining occurrences of the out-of-range value, and in response to determining a first occurrence, transmitting medical practitioner indicia selected from a first set of indicia corresponding to medical evaluations, and in response to determining a subsequent occurrence, transmitting medical practitioner indicia selected from a second set of indicia corresponding to medical recommendations.

5. The system of claim 1, further comprising a computer-aided manufacturing subsystem programmed to receive the design accommodation when generated by the design engine and manufacture the protective patient footwear corresponding to the design accommodation.

6. The system of claim 1, further comprising an image capture subsystem including a user interface and a lower extremity image capture device, the image capture subsystem adapted to receive digital input related to the lower extremity and generate an outputted design.

7. The system of claim 6, wherein the image capture subsystem comprises a scanning subsystem, and the image capture device comprises a scanner.

8. A computerized system for evaluation of protective patient footwear for a lower extremity, the system comprising:
   a design engine implemented on a computer having programmable memory and at least one processor that executes instructions stored in the programmable memory;
   at least one sensor positionable relative to the lower extremity to detect at least one physiologic parameter of the lower extremity, the physiologic parameter selected from the group consisting of plantar pressure, friction, temperature, force, force direction, contact area, acceleration, movement, moisture, temperature, and elapsed time;
   wherein the design engine is programmed to (a) receive input from the sensor corresponding to the physiologic parameter detected; (b) determine whether the input comprises an out-of-range value for the physiologic parameter; and (c) in response to the determination, generate an output to address the out-of-range value, the output consisting of at least one of a design accommodation and a treatment recommendation;
   wherein the design accommodation, when generated, corresponds to at least one of a proposed geometry and a proposed material of the protective patient footwear, and wherein the design accommodation is selected from a set of the design accommodations pre-programmed to correspond to the physiologic parameter for which the out-of-range value was detected; and
   wherein the protective patient footwear selected from the group consisting of a custom shoe, brace, boot, cast, corrective footwear, and an orthosis, wherein the design accommodation generated by the design engine corresponds to at least one accommodation selected from the group consisting of a substitution of alternate insole materials to account for a loss of elasticity or a lack of impact absorption, inclusion of friction-reducing insole top cover materials, and modification of insole dimensions associated with a location of the wound or ulceration.

9. A computerized system for evaluation of protective patient footwear for a lower extremity, the system comprising:
   a design engine implemented on a computer having programmable memory and at least one processor that executes instructions stored in the programmable memory;

at least one sensor positionable relative to the lower extremity to detect at least one physiologic parameter of the lower extremity, the physiologic parameter selected from the group consisting of plantar pressure, friction, temperature, force, force direction, contact area, acceleration, movement, moisture, temperature, and elapsed time;

wherein the design engine is programmed to (a) receive input from the sensor corresponding to the physiologic parameter detected; (b) determine whether the input comprises an out-of-range value for the physiologic parameter; and (c) in response to the determination, generate an output to address the out-of-range value, the output consisting of at least one of a design accommodation and a treatment recommendation; and a plurality of the sensors positioned on the protective patient footwear at predetermined sensor locations relative to a musculoskeletal structure of the lower extremity when the protective patient footwear is being worn.

10. The system of claim 9, for patient protective footwear comprising an insole, wherein the sensors are positioned relative to the insole to detect a plurality of the physiologic parameters of a plantar surface of the lower extremity when supported by the insole.

11. The system of claim 10, wherein, in response to the design engine determining that the out-of-range value at a first one of the sensor locations corresponds to the physiologic parameter of plantar pressure, the design accommodation, when generated by the design engine, is selected from the group consisting of an addition of material to increase the thickness of the insole at locations other than at the first location; a substitution of softer material at the first location; and inclusion of friction-reducing material at the top of the insole.

12. The system of claim 9, wherein the plurality of the sensors is programmed to determine a plurality of physiologic parameters, and wherein the design engine is programmed to (a) receive respective inputs from the sensors corresponding to each of the plurality of physiologic parameters; (b) identify at least a first input having an out-of-range value; (c) in response to the identification, employ the first input as a variable in the generation of the output to address the out-of-range value.

13. A computerized system for evaluation of protective patient footwear for a lower extremity, the system comprising:
a design engine implemented on a computer having programmable memory and at least one processor that executes instructions stored in the programmable memory;
at least one sensor positionable relative to the lower extremity to detect at least one physiologic parameter of the lower extremity, the physiologic parameter selected from the group consisting of plantar pressure, friction, temperature, force, force direction, contact area, acceleration, movement, moisture, temperature, and elapsed time;
wherein the design engine is programmed to (a) receive input from the sensor corresponding to the physiologic parameter detected; (b) determine whether the input comprises an out-of-range value for the physiologic parameter; and (c) in response to the determination, generate an output to address the out-of-range value, the output consisting of at least one of a design accommodation and a treatment recommendation; and
a patient interface, a plurality of the treatment recommendations, and first and second patient programming, the first patient programming adapted to transmit patient indicia corresponding to the treatment recommendation to the patient interface, the indicia comprising at least one patient recommendation selected from a first set of indicia of the patient recommendations;
wherein the second patient programming determines a previous occurrence of the out-of-range value and, in response, transmits patient indicia corresponding to the treatment recommendation and selected from a second set of indicia of the patient recommendations.

14. A computerized method for evaluating a lower extremity to be treated with protective patient footwear, the method comprising:
detecting at least one physiologic parameter of the lower extremity, the physiologic parameter selected from the group consisting of plantar pressure, friction, temperature, force, force direction, contact area, acceleration, movement, moisture, temperature and elapsed time;
receiving input corresponding to the physiologic parameter detected;
determining whether the input comprises an out-of-range value for the physiologic parameter; and
in response to the determination, generating an output to address the out-of-range value, wherein the output consists of at least one of a design accommodation and a treatment recommendation;
wherein the step of receiving input corresponding to the physiologic parameter comprises receiving a plurality of discreet inputs for a plurality of the physiologic parameters from a plurality of locations in operative proximity to the lower extremity;
wherein the step of determining the out-of-range value comprises determining the location of the out-of-range value relative to the lower extremity and the magnitude of the out-of-range value outside of a range value of the corresponding physiologic parameter; and
wherein the step of generating the output to address the out-of-range value comprises at least one processing operation using input selected from the group consisting of: physiologic parameters detected at locations other than the location associated with the out-of-range value, input corresponding to previous occurrences of the out-of-range values, gate analysis values, and input indicating existence of at least one medical condition.

15. The method of claim 14,
wherein the step of generating the output comprises generating at least one of the design accommodations selected from the group consisting of a proposed geometry for the protective patient footwear and a proposed material for the protective patient footwear;
wherein the step of generating output further comprises selecting the design accommodation from a pre-programmed set of the design accommodations associated with the physiologic parameter for which the out-of-range value was detected.

16. A computerized method for evaluating a lower extremity to be treated with protective patient footwear, the method comprising:
detecting at least one physiologic parameter of the lower extremity, the physiologic parameter selected from the group consisting of plantar pressure, friction, temperature, force, force direction, contact area, acceleration, movement, moisture, temperature and elapsed time;
receiving input corresponding to the physiologic parameter detected;
determining whether the input comprises an out-of-range value for the physiologic parameter; and in response to the determination, generating an output to address the out-of-range value, wherein the output consists of at least one of a design accommodation and a treatment recommendation;

wherein the step of generating output comprises generating the treatment recommendation by selection from a first set of indicia in response to determination of a first occurrence of the out-of-range value and from a second set of indicia in response to determination of a previous occurrence of the out-of-range value.

17. The method of claim 16, further comprising the step of transmitting the treatment recommendation to at least one of a patient user interface and a medical practitioner user interface.

* * * * *